US009198749B2

(12) United States Patent
Pathak

(10) Patent No.: US 9,198,749 B2
(45) Date of Patent: Dec. 1, 2015

(54) VASCULAR GRAFTS WITH MULTIPLE CHANNELS AND METHODS FOR MAKING

(75) Inventor: Chandrashekhar P. Pathak, Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1135 days.

(21) Appl. No.: 12/444,568

(22) PCT Filed: Oct. 12, 2007

(86) PCT No.: PCT/US2007/081261
§ 371 (c)(1),
(2), (4) Date: Apr. 6, 2009

(87) PCT Pub. No.: WO2008/063780
PCT Pub. Date: May 29, 2008

(65) Prior Publication Data
US 2010/0057196 A1 Mar. 4, 2010

Related U.S. Application Data

(60) Provisional application No. 60/829,247, filed on Oct. 12, 2006.

(51) Int. Cl.
*A61F 13/00* (2006.01)
*A61F 2/06* (2013.01)
*A61F 2/07* (2013.01)

(52) U.S. Cl.
CPC ... *A61F 2/06* (2013.01); *A61F 2/07* (2013.01); *A61F 2002/072* (2013.01); *A61F 2250/0068* (2013.01)

(58) Field of Classification Search
CPC ............... A61F 2/01; A61F 2002/016; A61F 2002/018; A61F 2002/065; A61F 2002/067; A61F 2002/068; A61F 2/06; A61F 2/064
USPC ................... 424/422–426; 604/264, 265, 267
See application file for complete search history.

(56) References Cited

U.S. PATENT DOCUMENTS

| | | | |
|---|---|---|---|
| 3,105,492 A | 10/1963 | Jeckel | |
| 3,677,800 A | 7/1972 | Wright | |
| 3,953,566 A | 4/1976 | Gore | |
| 3,962,153 A | 6/1976 | Gore | |
| 4,130,904 A | 12/1978 | Whalen | |
| 4,226,886 A * | 10/1980 | Lakes | 428/315.7 |
| RE31,618 E | 7/1984 | Mano et al. | |
| 4,550,447 A | 11/1985 | Seiler, Jr. et al. | |
| 4,604,762 A | 8/1986 | Robinson | |
| 4,619,641 A | 10/1986 | Schanzer | |
| 4,718,907 A | 1/1988 | Karwoski et al. | |
| 4,731,073 A | 3/1988 | Robinson | |
| 4,733,665 A | 3/1988 | Palmaz | |
| 4,739,013 A | 4/1988 | Pinchuk | |
| 4,743,252 A | 5/1988 | Martin, Jr. et al. | |
| 4,810,749 A | 3/1989 | Pinchuk | |
| 4,816,339 A | 3/1989 | Tu et al. | |
| 4,857,069 A | 8/1989 | Kira | |
| 4,880,002 A * | 11/1989 | MacGregor | 606/226 |
| 4,955,296 A | 9/1990 | Barlow | |
| 4,955,899 A | 9/1990 | Della Corna et al. | |
| 4,973,609 A | 11/1990 | Browne | |
| 4,990,138 A | 2/1991 | Bacich et al. | |
| 5,024,671 A * | 6/1991 | Tu et al. | 623/1.54 |
| 5,028,597 A | 7/1991 | Kodama et al. | |
| 5,061,276 A | 10/1991 | Tu et al. | |
| 5,102,402 A | 4/1992 | Dror et al. | |
| 5,116,360 A | 5/1992 | Pinchuk et al. | |
| 5,133,742 A | 7/1992 | Pinchuk | |
| 5,148,806 A | 9/1992 | Fukui et al. | |
| 5,152,782 A | 10/1992 | Kowligi et al. | |
| 5,192,310 A | 3/1993 | Herweck et al. | |
| 5,201,314 A | 4/1993 | Bosley, Jr. et al. | |
| 5,229,431 A | 7/1993 | Pinchuk | |
| 5,269,810 A | 12/1993 | Hull et al. | |
| 5,319,059 A | 6/1994 | Neuenschwander et al. | |
| 5,354,329 A | 10/1994 | Whalen | |
| 5,453,235 A | 9/1995 | Calcote et al. | |
| 5,462,781 A | 10/1995 | Zukowski | |
| 5,464,438 A | 11/1995 | Menaker | |
| 5,507,769 A | 4/1996 | Marin et al. | |
| 5,516,480 A | 5/1996 | Krall et al. | |
| 5,527,353 A | 6/1996 | Schmitt | |
| 5,556,426 A | 9/1996 | Popadiuk et al. | |
| 5,571,166 A | 11/1996 | Dinh et al. | |

(Continued)

FOREIGN PATENT DOCUMENTS

| | | | |
|---|---|---|---|
| CA | 2620487 A1 | 3/2007 | |
| EP | 0203833 A1 | 12/1986 | |

(Continued)

OTHER PUBLICATIONS

Sep. 24, 2008 International Search Report in international application PCT/US2007/081261.
Apr. 15, 2009 International Preliminary Report on Patentability in international application PCT/US2007/081261.
Aug. 27, 2008 Written Opinion of the International Searching Authority in international application PCT/US2007/081261.
Bard Peripheral Vascular, Dynaflo Bypass Grafts, Information for Use, Jan. 2005.
Bard Peripheral Vascular, Venaflo™ Vascular Grafts, Information for Use, Oct. 2004.
Graft. 2012. In TheFreeDictionary.com. Retrieved Aug. 22, 2012, from http://www.thefreedictionary.com/graft.
Hakimmehr, Dorna, The effect of organic solvents on sol-gel hydroxyapatite and its application as biocoating, The University of British Columbia, pp. 1-98, Oct. 2001.

(Continued)

*Primary Examiner* — Michael G Hartley
*Assistant Examiner* — Micah-Paul Young
(74) *Attorney, Agent, or Firm* — Buchalter Nemer

(57) ABSTRACT

A wall, for example the wall of a vascular graft, has multiple channels within it. The channels may be used to hold drugs or reinforcing fibers. The channels may have a predetermined roughness. The channels may be formed by coextrusion using a soluble material, for example, to define the channels and then dissolving them to open the channels in the extrudate.

8 Claims, 3 Drawing Sheets

(56) References Cited

U.S. PATENT DOCUMENTS

| | | |
|---|---|---|
| 5,605,696 A | 2/1997 | Eury et al. |
| 5,607,442 A | 3/1997 | Fischell et al. |
| 5,607,478 A | 3/1997 | Lentz et al. |
| 5,609,624 A | 3/1997 | Kalis |
| 5,620,763 A | 4/1997 | House et al. |
| 5,628,782 A | 5/1997 | Myers et al. |
| 5,628,786 A | 5/1997 | Banas et al. |
| 5,641,373 A | 6/1997 | Shannon et al. |
| 5,641,443 A | 6/1997 | Calcote et al. |
| 5,665,114 A | 9/1997 | Weadock et al. |
| 5,700,287 A | 12/1997 | Myers et al. |
| 5,707,386 A | 1/1998 | Schnepp-Pesch et al. |
| 5,711,960 A | 1/1998 | Shikinami |
| 5,716,393 A | 2/1998 | Lindenberg et al. |
| 5,716,395 A | 2/1998 | Myers et al. |
| 5,716,660 A | 2/1998 | Weadock et al. |
| 5,769,884 A * | 6/1998 | Solovay ............ 623/1.13 |
| 5,800,510 A | 9/1998 | Schmitt |
| 5,800,512 A | 9/1998 | Lentz et al. |
| 5,817,017 A | 10/1998 | Young et al. |
| 5,824,042 A | 10/1998 | Lombardi et al. |
| 5,824,050 A | 10/1998 | Karwoski et al. |
| 5,827,327 A | 10/1998 | McHaney et al. |
| 5,840,240 A | 11/1998 | Stenoien et al. |
| 5,843,171 A | 12/1998 | Campbell et al. |
| 5,843,173 A | 12/1998 | Shannon et al. |
| 5,851,229 A | 12/1998 | Lentz et al. |
| 5,851,230 A | 12/1998 | Weadock et al. |
| 5,860,999 A | 1/1999 | Schnepp-Pesch et al. |
| 5,861,026 A | 1/1999 | Harris et al. |
| 5,866,217 A | 2/1999 | Stenoien et al. |
| 5,893,840 A | 4/1999 | Hull et al. |
| 5,897,587 A * | 4/1999 | Martakos et al. ............ 623/1.13 |
| 5,904,967 A | 5/1999 | Ezaki et al. |
| 5,910,168 A | 6/1999 | Myers et al. |
| 5,931,865 A | 8/1999 | Silverman et al. |
| 5,972,027 A | 10/1999 | Johnson |
| 5,976,169 A | 11/1999 | Imran |
| 5,976,192 A | 11/1999 | McIntyre et al. |
| 6,001,125 A | 12/1999 | Golds et al. |
| 6,004,667 A | 12/1999 | Sakurada et al. |
| 6,010,529 A | 1/2000 | Herweck et al. |
| 6,019,787 A | 2/2000 | Richard et al. |
| 6,019,788 A | 2/2000 | Butters et al. |
| 6,022,335 A | 2/2000 | Ramadan |
| 6,027,779 A | 2/2000 | Campbell et al. |
| 6,036,724 A | 3/2000 | Lentz et al. |
| 6,039,755 A | 3/2000 | Edwin et al. |
| 6,042,666 A | 3/2000 | Karwoski et al. |
| 6,048,362 A | 4/2000 | Berg |
| 6,053,939 A | 4/2000 | Okuda et al. |
| 6,053,941 A | 4/2000 | Lindenberg et al. |
| 6,053,943 A | 4/2000 | Edwin et al. |
| 6,056,970 A | 5/2000 | Greenawalt et al. |
| 6,080,198 A | 6/2000 | Lentz et al. |
| 6,099,557 A | 8/2000 | Schmitt |
| 6,102,884 A | 8/2000 | Squitieri |
| 6,120,532 A | 9/2000 | Goldfarb |
| 6,124,523 A | 9/2000 | Banas et al. |
| 6,162,244 A | 12/2000 | Braun et al. |
| 6,174,330 B1 | 1/2001 | Stinson |
| 6,187,038 B1 | 2/2001 | Sullivan et al. |
| 6,187,039 B1 | 2/2001 | Hiles et al. |
| 6,187,054 B1 | 2/2001 | Colone et al. |
| 6,190,590 B1 | 2/2001 | Randall et al. |
| 6,200,338 B1 | 3/2001 | Solomon et al. |
| 6,203,568 B1 | 3/2001 | Lombardi et al. |
| 6,203,735 B1 | 3/2001 | Edwin et al. |
| 6,214,839 B1 | 4/2001 | Gutterer |
| 6,221,101 B1 | 4/2001 | Harris et al. |
| 6,253,769 B1 | 7/2001 | LaFontaine et al. |
| 6,261,257 B1 | 7/2001 | Uflacker et al. |
| 6,267,834 B1 | 7/2001 | Shannon et al. |
| 6,270,523 B1 | 8/2001 | Herweck et al. |
| 6,273,908 B1 | 8/2001 | Ndondo-Lay |
| 6,273,912 B1 | 8/2001 | Scholz et al. |
| 6,285,739 B1 | 9/2001 | Rudin et al. |
| 6,287,337 B1 | 9/2001 | Martakos et al. |
| 6,290,729 B1 | 9/2001 | Slepian et al. |
| 6,306,166 B1 | 10/2001 | Barry et al. |
| 6,315,791 B1 | 11/2001 | Gingras et al. |
| 6,319,279 B1 | 11/2001 | Shannon et al. |
| 6,328,762 B1 | 12/2001 | Anderson et al. |
| 6,355,063 B1 | 3/2002 | Calcote |
| 6,368,347 B1 | 4/2002 | Maini et al. |
| 6,379,381 B1 | 4/2002 | Hossainy et al. |
| 6,383,214 B1 | 5/2002 | Banas et al. |
| 6,383,215 B1 | 5/2002 | Sass |
| 6,398,806 B1 | 6/2002 | You |
| 6,416,537 B1 | 7/2002 | Martakos et al. |
| 6,426,114 B1 | 7/2002 | Troczynski et al. |
| 6,428,571 B1 | 8/2002 | Lentz et al. |
| 6,436,135 B1 | 8/2002 | Goldfarb |
| 6,443,981 B1 | 9/2002 | Colone et al. |
| 6,451,047 B2 | 9/2002 | McCrea et al. |
| 6,488,701 B1 | 12/2002 | Nolting et al. |
| 6,514,196 B1 | 2/2003 | Sullivan et al. |
| 6,534,084 B1 | 3/2003 | Vyakarnam et al. |
| 6,547,820 B1 | 4/2003 | Staudenmeier |
| 6,572,647 B1 | 6/2003 | Supper et al. |
| 6,589,278 B1 | 7/2003 | Harris et al. |
| 6,589,468 B1 | 7/2003 | Schmitt |
| 6,596,023 B1 | 7/2003 | Nunez et al. |
| 6,602,287 B1 | 8/2003 | Millare et al. |
| 6,660,301 B1 | 12/2003 | Vogel et al. |
| 6,663,664 B1 | 12/2003 | Pacetti |
| 6,673,102 B1 | 1/2004 | Vonesh et al. |
| 6,676,700 B1 | 1/2004 | Jacobs et al. |
| 6,712,919 B2 | 3/2004 | Ruefer et al. |
| 6,716,239 B2 | 4/2004 | Sowinski et al. |
| 6,719,783 B2 | 4/2004 | Lentz et al. |
| 6,726,696 B1 | 4/2004 | Houser et al. |
| 6,726,923 B2 | 4/2004 | Iyer et al. |
| 6,730,324 B2 | 5/2004 | Troczynski et al. |
| 6,746,480 B2 | 6/2004 | Scholz et al. |
| 6,756,007 B2 | 6/2004 | Pletzer et al. |
| 6,786,920 B2 | 9/2004 | Shannon et al. |
| 6,790,226 B2 | 9/2004 | Edwin et al. |
| 6,797,217 B2 | 9/2004 | McCrea et al. |
| 6,803,069 B2 | 10/2004 | Patnaik et al. |
| 6,814,753 B2 | 11/2004 | Schmitt |
| 6,821,295 B1 | 11/2004 | Farrar |
| 6,827,737 B2 | 12/2004 | Hill et al. |
| 6,863,686 B2 | 3/2005 | Shannon et al. |
| 6,926,735 B2 | 8/2005 | Henderson |
| 7,083,640 B2 | 8/2006 | Lombardi |
| 7,244,271 B2 | 7/2007 | Lentz et al. |
| 7,468,071 B2 | 12/2008 | Edwin et al. |
| 8,043,364 B2 | 10/2011 | Lombardi et al. |
| 8,066,758 B2 | 11/2011 | Bogert et al. |
| 8,313,524 B2 | 11/2012 | Edwin et al. |
| 2001/0018609 A1 | 8/2001 | Smith |
| 2001/0021870 A1 | 9/2001 | Edwin et al. |
| 2001/0029382 A1 | 10/2001 | Bowman et al. |
| 2002/0055097 A1 | 5/2002 | Polyak et al. |
| 2002/0065546 A1 | 5/2002 | Machan et al. |
| 2002/0065552 A1 | 5/2002 | Jayaraman et al. |
| 2002/0091439 A1 | 7/2002 | Baker et al. |
| 2002/0095157 A1 | 7/2002 | Bowman |
| 2002/0095205 A1 | 7/2002 | Edwin et al. |
| 2002/0127261 A1 | 9/2002 | Risbud et al. |
| 2002/0138048 A1 | 9/2002 | Tuch |
| 2002/0138136 A1 | 9/2002 | Chandresekaran et al. |
| 2002/0169465 A1 | 11/2002 | Bowman et al. |
| 2002/0193869 A1 | 12/2002 | Dang |
| 2002/0198559 A1 | 12/2002 | Mistry et al. |
| 2003/0004559 A1 | 1/2003 | Lentz et al. |
| 2003/0004563 A1 | 1/2003 | Jackson et al. |
| 2003/0017775 A1 | 1/2003 | Sowinski et al. |
| 2003/0027775 A1 | 2/2003 | Wallace |
| 2003/0028204 A1* | 2/2003 | Li et al. ............ 606/152 |
| 2003/0028240 A1 | 2/2003 | Nolting et al. |
| 2003/0060871 A1* | 3/2003 | Hill et al. ............ 623/1.15 |
| 2003/0100859 A1 | 5/2003 | Henderson et al. |

(56) References Cited

U.S. PATENT DOCUMENTS

| | | |
|---|---|---|
| 2003/0139799 A1 | 7/2003 | Ley et al. |
| 2003/0139806 A1 | 7/2003 | Haverkost et al. |
| 2003/0149471 A1 | 8/2003 | Briana et al. |
| 2003/0176915 A1 | 9/2003 | Wright et al. |
| 2003/0204242 A1 | 10/2003 | Zarins et al. |
| 2003/0216699 A1 | 11/2003 | Falotico |
| 2003/0224032 A1 | 12/2003 | Read et al. |
| 2004/0015228 A1 | 1/2004 | Lombardi et al. |
| 2004/0024442 A1 | 2/2004 | Sowinski et al. |
| 2004/0024456 A1 | 2/2004 | Brown et al. |
| 2004/0033364 A1 | 2/2004 | Spiridigliozzi et al. |
| 2004/0049264 A1 | 3/2004 | Sowinski et al. |
| 2004/0054406 A1 | 3/2004 | Dubson et al. |
| 2004/0064181 A1 | 4/2004 | Harris et al. |
| 2004/0076656 A1 | 4/2004 | Pavesio et al. |
| 2004/0078090 A1 | 4/2004 | Binette et al. |
| 2004/0082989 A1 | 4/2004 | Cook et al. |
| 2004/0117006 A1 | 6/2004 | Lewis et al. |
| 2004/0122507 A1 | 6/2004 | Henderson |
| 2004/0122509 A1 | 6/2004 | Brodeur |
| 2004/0127977 A1 | 7/2004 | Shanley |
| 2004/0146546 A1 | 7/2004 | Gravett et al. |
| 2004/0148013 A1 | 7/2004 | Epstein et al. |
| 2004/0164445 A1 | 8/2004 | Nieman et al. |
| 2004/0167572 A1 | 8/2004 | Roth et al. |
| 2004/0182511 A1 | 9/2004 | Rakos et al. |
| 2004/0186552 A1 | 9/2004 | St. Pierre |
| 2004/0186553 A1 | 9/2004 | Yan |
| 2004/0193242 A1 | 9/2004 | Lentz et al. |
| 2004/0210302 A1 | 10/2004 | Scholz et al. |
| 2004/0215337 A1 | 10/2004 | Hain et al. |
| 2004/0232588 A1 | 11/2004 | Edwin et al. |
| 2004/0236400 A1 | 11/2004 | Edwin et al. |
| 2004/0244442 A1 | 12/2004 | Shiao et al. |
| 2005/0002981 A1 | 1/2005 | Lahtinen et al. |
| 2005/0004653 A1 | 1/2005 | Gerberding et al. |
| 2005/0004661 A1 | 1/2005 | Lewis et al. |
| 2005/0010297 A1 | 1/2005 | Watson et al. |
| 2005/0015138 A1 | 1/2005 | Schuessler et al. |
| 2005/0015154 A1 | 1/2005 | Lindsey et al. |
| 2005/0055097 A1 | 3/2005 | Grunberg et al. |
| 2005/0060020 A1 | 3/2005 | Jenson |
| 2005/0064224 A1 | 3/2005 | Bavaro et al. |
| 2005/0096721 A1 | 5/2005 | Mangin et al. |
| 2005/0186243 A1 | 8/2005 | Hunter et al. |
| 2005/0246012 A1 | 11/2005 | Henderson |
| 2005/0283226 A1 | 12/2005 | Haverkost |
| 2006/0058867 A1 | 3/2006 | Thistle et al. |
| 2006/0116755 A1 | 6/2006 | Stinson |
| 2006/0259133 A1 | 11/2006 | Sowinski et al. |
| 2007/0038290 A1 | 2/2007 | Huang et al. |
| 2007/0123968 A1 | 5/2007 | Weinberg |
| 2007/0204445 A1 | 9/2007 | Hood et al. |
| 2007/0244539 A1 | 10/2007 | Lentz et al. |
| 2008/0027534 A1 | 1/2008 | Edwin et al. |
| 2008/0097349 A1* | 4/2008 | Dillinger .................. 604/265 |
| 2009/0171436 A1 | 7/2009 | Casanova et al. |
| 2010/0179642 A1 | 7/2010 | Bogert et al. |
| 2010/0268321 A1 | 10/2010 | McDermott et al. |
| 2011/0076315 A1 | 3/2011 | Casanova et al. |
| 2011/0125253 A1 | 5/2011 | Casanova et al. |
| 2012/0061001 A1 | 3/2012 | Bogert et al. |
| 2013/0071550 A1 | 3/2013 | Edwin et al. |

FOREIGN PATENT DOCUMENTS

| | | |
|---|---|---|
| EP | 0734721 A3 | 1/1997 |
| EP | 1371345 A2 | 12/2003 |
| EP | 1922025 A4 | 4/2012 |
| JP | 05-317408 A | 12/1993 |
| JP | 2000501961 A | 2/2000 |
| JP | 2000167063 A | 6/2000 |
| JP | 2000171595 A | 6/2000 |
| JP | 2000217903 A | 8/2000 |
| JP | 2002501779 T | 1/2002 |
| JP | 2002540854 T | 12/2002 |
| JP | 2003511196 A | 3/2003 |
| JP | 2003284781 A | 10/2003 |
| JP | 2004-537344 A | 12/2004 |
| JP | 2006511283 A | 4/2006 |
| JP | 2006514557 A | 5/2006 |
| JP | 2006527630 A | 12/2006 |
| JP | 2009506875 A | 2/2009 |
| JP | 5118042 | 10/2012 |
| WO | 9903036 A1 | 3/1990 |
| WO | 9323090 A1 | 11/1993 |
| WO | 9703812 A1 | 2/1997 |
| WO | 9721401 A1 | 6/1997 |
| WO | 9826731 A2 | 6/1998 |
| WO | 0128456 A1 | 4/2001 |
| WO | 0149340 A1 | 7/2001 |
| WO | 0158504 | 8/2001 |
| WO | 02055121 A1 | 7/2002 |
| WO | 02055122 A1 | 7/2002 |
| WO | 2004011055 A2 | 2/2004 |
| WO | 2004021931 A1 | 3/2004 |
| WO | 2004096307 A1 | 11/2004 |
| WO | 2006133373 A3 | 5/2007 |
| WO | 2007030512 A3 | 6/2007 |

OTHER PUBLICATIONS

Ignjatovic, Nenad, et al., Hydroxyapatite/poly-L-lactide (Collagen) Biocomposite with Poly-L-lactide of Different Molecular Weights, Advanced Engineering Materials, 2, No. 8 (2000), pp. 511-514.

JP Application No. 2008-515934 filed Dec. 7, 2007 Office Action dated Mar. 13, 2012.

JP Application No. 2008-515934 filed Dec. 7, 2007 Office Action dated May 6, 2011.

Masaki, Takahisha, et al., In Vitro Pharmacological Inhibition of Human Vascular Smooth Muscle Cell Proliferation for the Prevention of Hemodialysis Vascular Access Stenosis, Blood Purification, vol. 22, No. 3, pp. 307-312 (2004).

PCT/US2006/022359 filed Jun. 8, 2006 International Preliminary Report on Patentability dated Dec. 11, 2007.

PCT/US2006/022359 filed Jun. 8, 2006 International Search Report dated Mar. 1, 2007.

PCT/US2006/022359 filed Jun. 8, 2006 Written Opinion dated Mar. 1, 2007.

PCT/US2006/034671 filed Sep. 5, 2006 International Preliminary Report on Patentability dated Mar. 11, 2008.

PCT/US2006/034671 filed Sep. 5, 2006 International Search Report dated Apr. 2, 2007.

PCT/US2006/034671 filed Sep. 5, 2006 Written Opinion dated Apr. 2, 2007.

Ravaglioli, A., et al., Performances of Hydroxyapatite Porosity in Contact with Cells and Tissues, Key Engineering Materials, vols. 254-256, pp. 1017-1020 (2004).

U.S. Appl. No. 11/916,813, filed Aug. 27, 2010 Non-Final Office Action dated Apr. 9, 2012.

U.S. Appl. No. 11/916,813, filed Aug. 27, 2010 Non-Final Office Action dated Aug. 30, 2012.

U.S. Appl. No. 12/065,888, filed Jun. 9, 2010 Non-Final Office Action dated Jul. 17, 2012.

W. L. Gore & Associates, Inc., Gore-Tex® Intering Vascular Graft Advertisement, 2 pages, Aug. 2004.

W. L. Gore & Associates, Inc., The Highway of Life Advertisement, 2 pages, May 2004.

EP 05855344.7 filed Dec. 28, 2005 Examination Report dated Oct. 26, 2012.

EP 05855344.7 filed Dec. 28, 2005 Extended European Search Report dated Aug. 14, 2012.

EP 06772602.6 European Search Report dated Jan. 4, 2013.

EP 06839787.6 filed on Nov. 11, 2006 EP Search Report dated Jan. 12, 2010.

EP 06839788.4 filed on Aug. 5, 2008 EP Search Report dated Dec. 28, 2009.

EP 06839788.4 filed on Aug. 5, 2008 Office Action dated Jul. 13, 2010.

(56) References Cited

OTHER PUBLICATIONS

James et al, "In Vivo Patency of Endothelial Cell-Lined ePTFE Prostheses in an Ovine Model"; Artif Organs, Aug. 16, 1992(4):346-53.
JP 2007-530364 filed Aug. 30, 2005 Office Action dated Oct. 19, 2010.
JP 2008-516811 filed Dec. 28, 2005 Office Action dated Mar. 28, 2011.
JP 2008-540337 filed Apr. 27, 2006 Office Action dated Apr. 6, 2012.
JP 2008-540337 filed Apr. 27, 2006 Office Action dated Nov. 24, 2011.
JP 2008-540338 filed Apr. 27, 2006 Office Action dated Sep. 30, 2011.
Kohler et al, "Dialysis Access Failure: A Sheep Model of Rapid Stenosis", J Vasc Surg., Oct. 30, 1999(4):744-51.
Murase, Katsutoshi et al: "Graft-preserving treatment for vascular graft infected with Staphylococcus aureus with antibiotic-releasing porous apatite ceramic in the rabbit", Journal of Vascular Surgery, v. 38, No. 2, Aug. 1, 2003, pp. 368-373.
PCT/US2005/031186 filed Aug. 30, 2005 International Preliminary Report on Patentability dated Feb. 28, 2007.
PCT/US2005/031186 filed Aug. 30, 2005 Search Report dated Feb. 6, 2007.
PCT/US2005/031186 filed Aug. 30, 2005 Written Opinion dated Feb. 6, 2007.
PCT/US2005/046763 filed Dec. 28, 2005 International Preliminary Report on Patentability dated Dec. 17, 2007.
PCT/US2005/046763 filed Dec. 28, 2005 Search Report dated Apr. 30, 2007.
PCT/US2005/046763 filed Dec. 28, 2005 Written Opinion dated Apr. 30, 2007.
PCT/US2006/060702 filed on Nov. 11, 2006 International Preliminary Report on Patentability dated May 14, 2008.
PCT/US2006/060702 filed on Nov. 11, 2006 Search Report dated Dec. 28, 2007.
PCT/US2006/060702 filed on Nov. 11, 2006 Written Opinion dated Dec. 28, 2007.
PCT/US2006/060704 filed on Nov. 9, 2006 International Preliminary Report on Patentability dated May 14, 2006.
PCT/US2006/060704 filed on Nov. 9, 2006 Search Report dated Nov. 1, 2007.
PCT/US2006/060704 filed on Nov. 9, 2006 Written Opinion dated Nov. 1, 2007.
Tillman et al, "Platelet Function and Coagulation Parameters in Sheep During Experimental Vascular Surgery", Lab Anim Sci., Jun. 1981; 31 (3):263-7.
U.S. Appl. No. 11/661,250, filed Mar. 27, 2007 Final Office Action dated Oct. 14, 2009.
U.S. Appl. No. 11/661,250, filed Mar. 27, 2007 Non-Final Office Action dated Apr. 1, 2009.
U.S. Appl. No. 11/661,250, filed Mar. 27, 2007 Non-Final Office Action dated Apr. 13, 2012.
U.S. Appl. No. 11/661,250, filed Mar. 27, 2007 Non-Final Office Action dated Sep. 18, 2008.
U.S. Appl. No. 11/661,250, filed Mar. 27, 2007 Notice of Allowance dated Jul. 27, 2012.
U.S. Appl. No. 11/916,813, filed Aug. 27, 2010 Final Office Action dated Jan. 10, 2013.
U.S. Appl. No. 11/917,135, filed Jan. 17, 2008 Final Office Action dated May 9, 2011.
U.S. Appl. No. 11/917,135, filed Jan. 17, 2008 Non-Final Office Action dated Nov. 26, 2010.
U.S. Appl. No. 12/065,888, filed Jun. 9, 2010 Final Office Action dated Mar. 7, 2013.
U.S. Appl. No. 12/092,561, filed Sep. 17, 2008 Final Office Action dated Jun. 15, 2012.
U.S. Appl. No. 12/092,561, filed Sep. 17, 2008 Non-Final Office Action dated Jan. 4, 2012.
U.S. Appl. No. 12/092,636, filed Sep. 12, 2008 Non-Final Office Action dated Nov. 15, 2012.

* cited by examiner

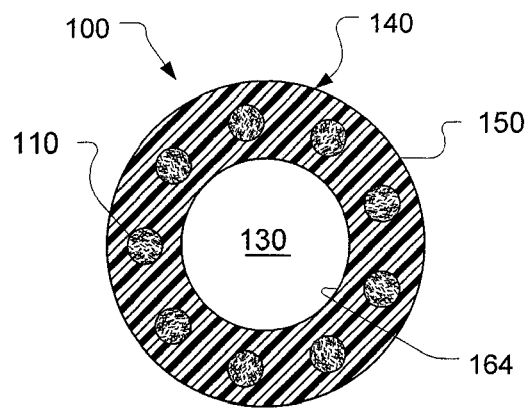
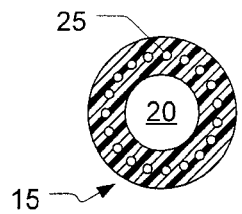
Fig. 2A
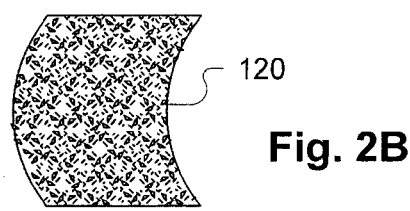
Fig. 2B
Fig. 1A
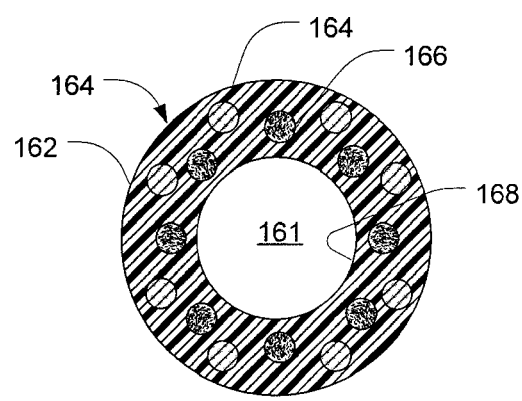
Fig. 1B
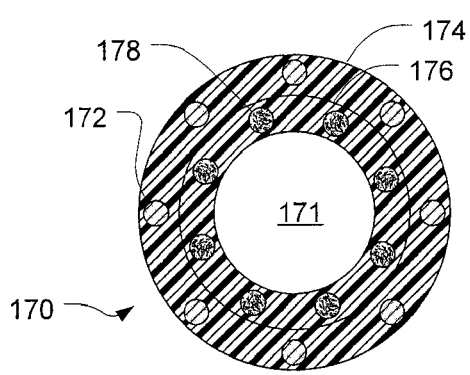
Fig. 1C
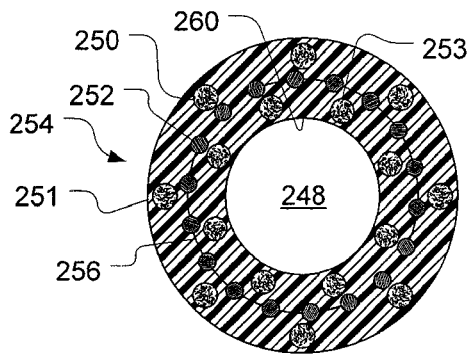
Fig. 1D
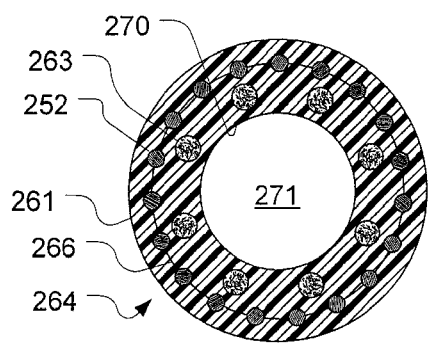
Fig. 1E

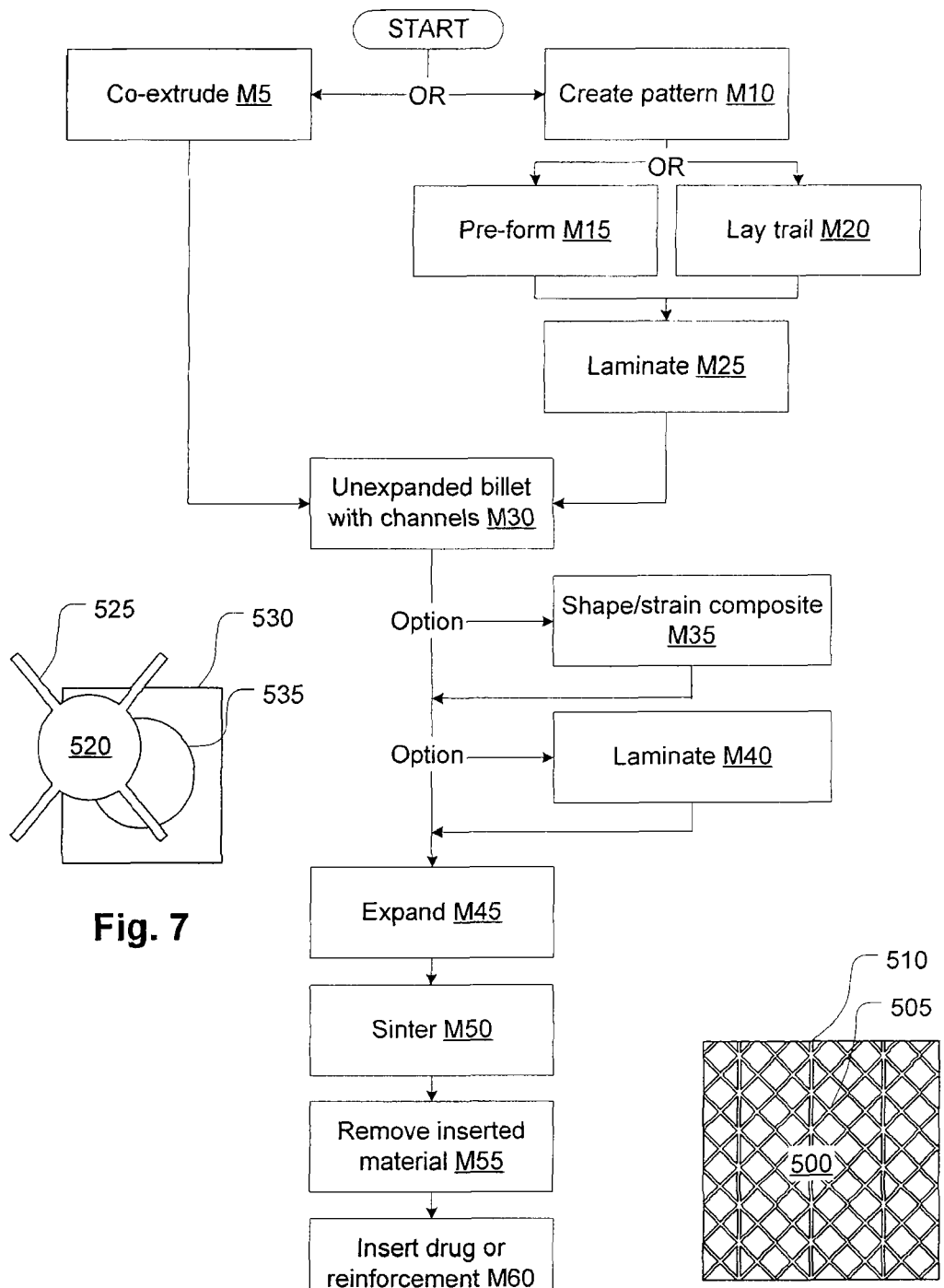
Fig. 5
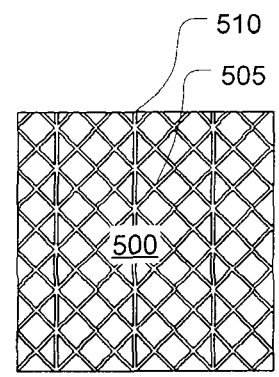
Fig. 7
Fig. 6

VASCULAR GRAFTS WITH MULTIPLE CHANNELS AND METHODS FOR MAKING

PRIORITY CLAIM AND INCORPORATION BY REFERENCE

This application is a U.S. national stage application under 35 USC §371 of International Application No. PCT/US2007/081261, filed Oct. 12, 2007, which claims benefit of priority to U.S. Provisional Patent Application No. 60/829,247, filed Oct. 12, 2006, each of which is hereby incorporated by reference in its entirety into this application.

TECHNICAL FIELD

The present invention relates to medical devices, such as grafts and methods of making the same. More particularly, it relates to such devices with multiple channels in a wall of the device. The invention also relates such devices where the multiple channels are used for drug delivery and reinforcement and methods for making the same of biocompatible polymers, such as expanded polytetrafluoroethylene (ePTFE).

BACKGROUND ART

Implantable prostheses, such as vascular grafts, are commonly used in medical procedures. Tubular grafts may be used to replace or repair damaged or diseased blood vessels. The effectiveness of such devices depends on a number of factors. Important among these are the factors that allow prostheses to match the characteristics of the natural body tissue that is being repaired or replaced, or to adequately compensate for any the prosthesis's shortcomings. In addition, prostheses may exceed the performance of the body part being replaced or repaired, in some respects, or provide some auxiliary function not normally associated with the replaced body part to be replaced or repaired but which may be useful in treating disease or injury.

It is well known to use extruded tubes of polytetrafluoroethylene (PTFE) to make vascular grafts. PTFE is suitable as an implantable prosthesis because of its biocompatibility. PTFE tubes, used as vascular grafts, generally exhibit low thrombogenicity. In vascular applications, the grafts are manufactured from expanded polytetrafluoroethylene (ePTFE) tubes. The microporous structure of these tubes permits natural tissue ingrowth once implanted in a living host. This contributes to healing and long-term patency.

Grafts of ePTFE have a fibrous structure with interspaced nodes connected by fibrils. Where the spaces between the node surfaces are large, tissue ingrowth and cell endothelization may be enhanced. But this characteristic also tends to make the graft delicate. So a number of prior art techniques to reinforce such grafts have been proposed.

One approach has been to modify the structure of the extruded PTFE tubing, during formation, to align fibrils, thereby increasing both radial tensile strength as well as axial tear strength. Forming tubular grafts of multiple layers using different material structures where one tubular structure is formed about another can provide the strength of one material with the porosity and endothelization effectiveness of the other material. Combinations of PTFE and textiles or metal mesh, as used in stents, are known.

With regard to ePTFE grafts, it is known to incorporate antimicrobial agents to form a coating composition which may include a biodegradable polymer and anti-microbial agents, for example, chlorhexidine acetate and pipracil. Known stents or vascular prostheses include those with an overlying biodegradable coating layers that contain drugs, such as anti-coagulants or antibiotic substances. Also known are medical implants where an antimicrobial agent is impregnated throughout the material of the implant or in a region near the surface. Silver may be deposited onto the surface of a porous polymeric substrate via beam deposition and then the pores may be filled with a polymeric material that is biodegradable.

Also known is an implantable graft, with inner and outer coaxial tubes with a space between them separated by ribs. The primary and secondary tubular bodies are joined by the ribs and may be bonded or extruded. The spaces between the tubes can be filled with a leak sealing agent or drug.

There is a need in the art for improved methods of manufacturing multi-channel grafts and also for providing such grafts with certain surface characteristics in the wall-channels.

In the prior art, ePTFE based grafts are typically subjected to a sintering process which is generally done at high temperatures (>100°). Such high temperature exposure can reduce or destroy the bioactivity of many bioactive substances. In addition, there is a need to develop graft-based drug delivery technologies that can provide for drug delivery without altering the surface characteristics of ePTFE grafts.

DISCLOSURE OF INVENTION

Briefly, a wall structure, which can be a portion or entirety of various kinds of medical device, for example the wall of a vascular graft, has multiple channels within it. The channels are be used to hold drugs, reinforcing fibers, or other materials such as leak sealant. The channels have a predetermined roughness and are formed by coextrusion using a soluble material, for example, to define the channels and then dissolving them to open the channels in the extrudate.

According to an embodiment, a method of forming a medical device is provided. The medical device may be a graft, for example. The method includes forming an extruded article by co-extruding a first material and a second material, such that, after extrusion, the second material defines at least one enclosed elongate structure surrounded by the matrix of the first material and then removing the second material by subjecting the extruded article to a cleaning process that causes the second material to flow out of the first material.

The second material is preferably a granular material and, in a particular embodiment, the particle size is limited to not more than 100 µm. The second material is preferably a soluble material where the cleaning process involves simply dissolving the soluble material. A preferred example of a soluble material is a salt, such as sodium chloride. Preferably, the method includes expanding the first material after removing the second material. The method preferably further includes sintering the first material after expanding it. The first material is preferably a polymer, more preferably, a thermopolymer, and even more preferably, polytetrafluoroethylene.

In another embodiment, voids left in the first material of the most general embodiment above can be filled with a drug. The voids left in the first material, after removal of the second material, can be filled with an antithrombogenic drug. The method can include filling the voids left in the first material, after removal of the second material, with a drug/polymer mixture filling them with reinforcement filaments. The extruded article could be shaped in any suitable manner including a cylinder, a patch, a cone, etc. The article can be twisted to cause the channels to be curved. For example, if an article is shaped as a tube, then twisting it can cause the channels to be helically shaped.

According to another embodiment, a medical device is provided, which may be a graft, with a wall of biocompatible polymer that has multiple channels within the wall. The interior surfaces of the channels have a roughness of at least 50 µm. The wall can be either cylindrical or generally planar, depending on the kind of article. The wall is of ePTFE in an exemplary embodiment. The channels allow the article to be reinforced using reinforcing filaments in the channels. Also they can be used to alter the behavior such as when nitinol wires are in threaded into the channels. The channels can be helical. The channels can also be filled with a drug or a drug/polymer mixture. For example, the drug could be an antithrombogenic drug.

According to another embodiment, a medical device is provided, for example, a graft, with a wall of biocompatible polymer that has multiple channels within the wall. The channels have a diameter of at least 50 µm and less than 1000 µm. The wall can be either cylindrical or generally planar, depending on the kind of article. The wall is of ePTFE in an exemplary embodiment. The channels allow the article to be reinforced using reinforcing filaments in the channels. Also they can be used to alter the behavior such as when nitinol wires are in threaded into the channels. The channels can be helical. The channels can also be filled with a drug or a drug/polymer mixture. For example, the drug could be an antithrombogenic drug.

According to another embodiment, a medical device is provided, for example, a graft, with a wall of biocompatible polymer that has multiple channels within the wall. The channels have circular cross-sections. Preferably, the channels have a diameter of at least 50 µm and less than 1000 µm. The wall can be either cylindrical or generally planar, depending on the kind of article. The wall is of ePTFE in an exemplary embodiment. The channels allow the article to be reinforced using reinforcing filaments in the channels. Also they can be used to alter the behavior such as when nitinol wires are in threaded into the channels. The channels can be helical. The channels can also be filled with a drug or a drug/polymer mixture. For example, the drug could be an antithrombogenic drug.

According to another embodiment, a medical device is provided, for example, a graft. For this and all disclosed embodiments, the graft can be any type of article for implantation in living tissue without regard to its particular function. Examples of grafts are cardiac patches, hernia patches, vascular grafts including reinforcements for blood vessels and temporary blood vessels. Grafts can also include, for example, orthopedic grafts such as bone reinforcements. Grafts can also include, for example, temporary skin for burns. The method for making the graft, in the present embodiment, includes forming an extruded article by co-extruding a first material and a second material, such that, after extrusion, the second material defines at least one enclosed elongate structure surrounded by the matrix of the first material. The method further includes removing the second material by subjecting the extruded article to a cleaning process that causes the second material to flow out of the first material.

In a variation of the method the second material is a granular material and in a further embodiment the granular material has a particle size of not more than 100 µm. Preferably, removable material is a soluble material and the cleaning process includes dissolving the soluble material. The soluble material, more preferably, may include salt, such as sodium chloride.

In another preferred embodiment, the method further includes expanding the first material after removing the second material. After that, preferably, the first material is sintered. The first material can include, or be, a polymer and preferably, a thermopolymer, and also preferably, the first material is a biocompatible polymer such as PTFE.

In a more preferred embodiment, the first embodiment method is combined with operation of filling voids left in the first material, in a preferred example, PTFE, after removal of the second material, with a drug or a reinforcement. Drugs such as an antithrombogenic drug may be used, for example. In many embodiments, drugs are preferably drug/polymer mixtures, or microencapsulated drugs. In a preferred embodiment, the graft is cylindrical. The method may include twisting the cylinder to make the channels into helices.

According to another embodiment, a medical device is provided, with a wall of biocompatible polymer having multiple channels within the wall. The interior surfaces of the channels having a roughness of at least 50 µm and, for some embodiments, the roughness is more preferably, at least 100 µm. In a preferred embodiment, the wall is cylindrical and in another, it is planar.

In another embodiment, the graft is reinforced by inserting or threading wires or other reinforcing members into the graft. A preferred example is nitinol. The channels may be formed into helices. The channels can wind in respective opposite directions in separate layers that are laminated together in the graft. In these and the earlier embodiments, the channels can be filled with a drug or drug mixture. Examples of drugs include antithrombogenic drugs (e.g., heparin, PPACK, enoxaprin, aspirin, coumadin, hirudin, TPA, urokinase, and streptokinase), immunologically stimulating drugs, anti restenosis drugs, systemic drugs, medicaments, anaesthetic drugs, etc.

According to another embodiment, a graft has a wall of porous hydrophobic biocompatible thermopolymer with edges. The wall has channels formed in it with diameters of at least 50 µm which are continuous from a point proximal at least one of the edges to a point remote from the edge. The channels are substantially filled a drug composition including a drug in a bioactive condition, which drug is of such a composition as to become non-bioactive if subjected to the temperatures required to sinter the thermopolymer.

In various preferred embodiments, the diameters are less than 1000 µm, the channels have an interior surface roughness that is substantially larger than the size of the largest pores in the porous thermopolymer, and the channels contain a non-drug material which microencapsulates the drug.

In one preferred embodiment, the channels are free of any other material but in a particular embodiment in which drugs are administered by the graft, the channels contain a fiber impregnated with the drug. Preferably, the thermopolymer includes PTFE and the wall is even more preferably expanded PTFE.

In another preferred embodiment, the graft has a stent encapsulated by, and isolated from the channels by the thermoplastic. The stent may define a continuous layer owing to the construction by lamination.

According to yet another embodiment, a graft has a wall of porous hydrophobic biocompatible thermopolymer having edges and channels formed therein. The channels have diameters of at least 50 µm and less than 1000 µm. The channels are substantially filled a drug composition including a drug in a bioactive condition, which drug is of such a composition as to become non-bioactive if subjected to the temperatures required to sinter the thermopolymer.

In a preferred version of the above embodiment, the channels have an interior surface roughness that is substantially larger than the size of the largest pores in the porous thermopolymer. The graft can be shaped as a cylinder, a patch, or similar article. The channels may be used to contain a non-drug material which microencapsulates the drug, a pure drug, a drug mixed with polymer or other material such as a fiber, a reinforcement or other materials. Preferably the thermopolymer is, or includes, PTFE and more preferably it is in an expanded condition making it sufficiently porous that, where the channels have a drug, the drug can pass through the pores into the host tissue. In a particular variation, the graft includes a stent isolated from the channels by the thermoplastic. The stent may define a continuous layer.

According to yet another embodiment, a graft has a wall of porous hydrophobic biocompatible thermopolymer having edges and channels formed therein with diameters of at least 50 µm, less than 1000 µm. The channels are substantially filled a drug composition including a drug in a bioactive condition, which drug is of such a composition as to become non-bioactive if subjected to the temperatures required to sinter the thermopolymer. Finally, in this embodiment, the stent is encapsulated by, and isolated from the channels, by the thermoplastic.

In a preferred version of the above embodiment, the channels have an interior surface roughness that is substantially larger than the size of the largest pores in the porous thermopolymer. The graft can be shaped as a cylinder, a patch, or similar article. The channels may be used to contain a non-drug material which microencapsulates the drug, a pure drug, a drug mixed with polymer or other material such as a fiber, a reinforcement or other materials. Preferably the thermopolymer is, or includes, PTFE and more preferably it is in an expanded condition making it sufficiently porous that, where the channels have a drug, the drug can pass through the pores into the host tissue. In a particular variation, the graft includes a stent isolated from the channels by the thermoplastic. The stent may define a continuous layer.

According to yet another embodiment, a method begins by expanding billet of hydrophobic biocompatible thermopolymer having channels filled with a soluble granular material. Then the expanded billet is thermally fixed in its expanded state to create a microporous structure. This method can further include dissolving the granular material to leave the article channels empty of the granular material. The granular material may be salt, plastic, glass, metal, fiber, or other material and the thermopolymer is preferably PTFE. In a preferred embodiment, the channels have diameters of at least 50 µm and less than 1000 µm, and are substantially filled a drug composition including a drug in a bioactive condition. The drug can be of such a composition as to become non-bioactive if subjected to the temperatures required to sinter the thermopolymer. The particle size of the granular material is preferably smaller than 100 µm. Preferably, in a further operation, the thermopolymer is thermally fixed by sintering.

More preferably, the method includes filling the channels with a drug, which may include threading a fiber impregnated with a drug through the channels, injecting with a hypodermic needle, microencapsulating the drug, and even soaking the drug through the material until it fills the channels and later washing the surface free of the drug while leaving drug within the graft.

In a further refinement of the method, the billet is formed by co-extruding a thermopolymer and a granular material. The billet may include a stent enveloped by the thermopolymer by laminating more than one graft with channels over another graft. In this case, preferably, the stent is enveloped by the thermopolymer and the method further includes filling the channels with a drug.

In all of the foregoing methods, there are many materials that can be incorporated in a billet (including an expanded billet) and used with the various embodiments of the methods. Examples of these include, but are not limited to, hyaluronic acid, polyethylene-oxide, polyvinyl-alcohol, dextran, gelatin, and cellulose. As for drugs or other agents that may be used in the channels of the grafts of all of the various embodiments described in the present disclosure, examples include antithrombogenic drugs (e.g., heparin, PPACK, enoxaprin, aspirin, coumadin, hirudin, TPA, urokinase, and streptokinase), immunologically stimulating drugs, anti restenosis drugs, systemic drugs, medicaments, etc.

In all of the foregoing embodiments, and those described elsewhere in the specification, where stents are incorporated in the graft, there are a variety of different kinds of stents that may be used. For example, one structure is shown in U.S. Pat. No. 7,083,640, which is hereby incorporated by reference in its entirety.

In all of the embodiments drugs may be used in the channels or voids, as mentioned. In such embodiments, a particularly useful class of drugs is anesthetics. Grafts are often attached to, or positioned close to, traumatized tissue. The trauma may be a result of the attachment of the graft or as a result of another related or unrelated procedure. By including an anesthetic, alone, or in combination with other drugs or reinforcement materials in the sub-channels or chambers, the effects of the trauma can be mitigated. Also the anesthetic can be delivered in a manner that concentrates it where it is needed most.

In addition to graft embodiments, the embodiments include non-graft devices such as patches or cylinders or other extrudable shapes can be used purely for the purpose of delivering one or more drugs to a site within a living host. For example, such a device may be removable, such as a drain left in a patient after surgery to allow fluid to exit. Such a drain may deliver drugs or be reinforced in the manner described in the instant application. Also, the device need not serve a function other than drug-delivery. For example, it may be left in a patient purely for the purpose of delivering drugs without serving an additional function, such as one of a graft. Other examples of non-graft devices are long and short-term catheters.

All of the embodiments may be combined with other devices. This is so, even in such combinations that cause another article to come between the embodiment and the host tissue. For example, a cylindrical medical device with sub-channels that hold drugs may be placed over a catheter or graft whose interior contacts blood or other fluids from the host and the medical device with the sub-channels is attached to provide a vehicle for drug delivery.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

FIG. 1A shows, in section, a vascular graft according to an embodiment of the invention in which drug-filled lumens are provided in a wall of the graft.

FIG. 1B shows, in section, a vascular graft according to an embodiment of the invention in which drug-filled and reinforcement-filled lumens are provided in a wall of the graft.

FIG. 1C shows, in section, a vascular graft according to an embodiment of the invention in which drug-filled and reinforcement-filled lumens are provided in laminated layers forming a wall of the graft.

FIG. 1D shows, in section, a vascular graft according to an embodiment of the invention in which drug-filled lumens are provided in a wall layers that are laminated over a stent.

FIG. 1E shows, in section, a vascular graft according to an embodiment of the invention in which drug-filled lumens are provided in a wall layer and a monolithic layer that are laminated over opposite surfaces of a stent.

FIG. 2A illustrates an expanded billet used to form embodiments of the invention.

FIG. 2B figuratively illustrates a rough surface of a sub-channel produced by a method of co-extruding a graft.

FIG. 5 illustrates a flow chart for use in discussing various embodiments of methods for forming grafts.

FIG. 6 shows a lattice structure that may be used according to an embodiment of a method for making a graft.

FIG. 7 shows a detail of a channel structure that provides capsules within the wall structure of a graft.

MODE(S) FOR CARRYING OUT THE INVENTION

Figure 3A:
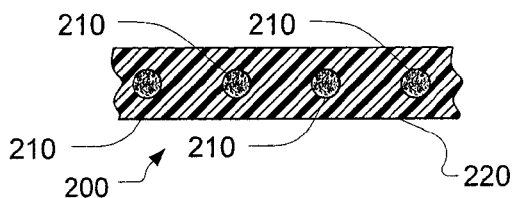
FIGS. 3A and 3B show portions of respective grafts having generally planar wall structures or alternatively, they may represent the walls of shaped structures such as a tubular structure as shown in FIG. 2.

Referring to FIG. 1A, a round graft 100 is shown in cross-section. A wall 140 of the graft 100 is preferably primarily of expanded Polytetrafluoroethylene (ePTFE) or similar biocompatible material and contains a channel 130 and multiple sub-channels 110. Although not shown, the channel 130 and sub-channels 110 run longitudinally along the length of the graft 100. The sub-channels 110 can be curved, but they extend generally along the length of the graft 100. Note that in the figures are the dimensions and proportions are exaggerated for clarity.

The channels 110 are, in this embodiment, filled with a drug, such as an anticoagulant, but the sub-channels 110 could also contain reinforcements. Although four sub-channels are shown, the number can be chosen to suit the application and designer preferences. A wall 140 defines the channel 130 and sub-channels 110. In the embodiments in which a drug is incorporated in the sub-channels 110, the drug flows through the porous medium of the expanded polymer material (e.g., ePTFE) that makes up the matrix of the wall 140.

The graft 100 and other embodiments shown in FIGS. 1A to 1E are examples of structures suitable for vascular grafts and/or stent grafts, but the embodiments are not necessarily limited to grafts, tubular grafts, or stent grafts. For example, FIGS. 3A and 3B, discussed below, illustrate planar structures 220 and 226 with sub-channels 210, 211, 212 which might be suitable, for example for vascular grafts, stent coverings, cardiovascular patches, facial implants, ventricular assist device components, or other implantable devices in addition to vascular grafts and stent coverings.

Focusing again on FIG. 1A, the sub-channels 110 may be filled with drugs and/or metal or fiber reinforcements, nitinol wires, or other materials to make a graft or stent graft. The drug or drug/polymer mixture may be isolated from the tissue-contacting or blood-contacting surfaces of the graft 100 so as not to affect the desirable properties of the tissue-contacting or blood-contacting surfaces, for example abluminal 150 and luminal 164 surfaces. These surfaces are preferably of biocompatible or non-thrombogenic materials such as PTFE. In addition, the textures of the tissue-contacting or blood-contacting surfaces of the graft 100 such as the abluminal 150 and luminal 164 surfaces are unaffected, or minimally affected, by the texture of the material contained in the sub-channels 110.

Referring to FIG. 2A, as explained in more detail below, the graft 100 of FIG. 1A may be made by co-extruding PTFE and granular salt, where the salt defines the sub-channels 110 to form a billet. The billet may then be expanded and sintered and the salt removed, for example by dissolving with water, to form an article 15 (i.e., the expanded billet) with open sub-channels 25. The drug may be inserted in the sub-channels 25, for example, by injecting microsphere-encapulated drug particles or by threading a drug-impregnated fiber through the sub-channels 110.

Referring now to FIG. 2B, as a result of the use of granular material used to define the channels, the internal surfaces of the channels 110, a section of which is represented at 120, have a roughness corresponding to the grain size of the granular material used. It is believed that this makes the transfer of drugs through wall 140 matrix faster and more complete than a smooth internal surface. This roughness can be controlled by selection of the particle size distribution of the granular material used to define the sub-channels.

The sub-channels 110 of FIG. 1A are shown as a polar array, but it should be clear than any desired spacing, number, size, and arrangement of the sub-channels can be provided. Referring now to FIG. 1B, for example, sub-channels 164, 166 are staggered and different materials are inserted in the sub-channels 164, 166, in this case, metal reinforcements 164 (which may also be fiber or other materials) and drugs or medicaments as indicated at 166. The embodiments of FIG. 1A or 1B can be provided by using the extrusion method described above, with a material that can tolerate the expanding and sintering operations processes and may be co-extruded with the PTFE (or other polymer) and do not need to be removed in a later operation. Alternatively, the sintering process and/or the expansion process can be performed after removing thee co-extruded material. Also, the removal operation can be skipped altogether if the material can remain. For example, in the FIG. 1B embodiment, the metal reinforcements 164 may be co-extruded with the PTFE (or other polymer) and left in place.

FIG. 1C represents another structure in which two coaxial layers 174 and 176, each similar to the graft 100 of FIG. 1A, are laminated to each other. In this embodiment, an outer array of sub-channels 172, which carry metallic reinforcement filaments, is contained in an outer annular layer 174. An inner array of sub-channels 178, which carry a drug or medicament, is contained in an outer annular layer 176. A preferred method of forming this embodiment is to provide two cylindrical billets as shown in FIG. 2A and to place each in turn over a mandrel with the outer layer over the inner layer. The two billets are then bonded together, for example by sintering, to form layers of a single wall. Then the two bonded layers are expanded, sintered, the material removed used to create the sub-channels 172 (e.g. salt) and the reinforcing material threaded into the channels and the drug material inserted into the sub-channels 178.

FIGS. 1D and 1E show embodiments in which two layers of biocompatible material, such as PTFE are laminated together with another structure 252, such as a stent, sandwiched between them.

The embodiment 254 has an outer layer outer layer 251 and an inner layer 256, each being a composite with drug-containing sub-channels 250, 253. The inner layer 256 defines a channel 248. The other structure 252, which in a preferred embodiment, is a stent, is secured between the composite structure layers 251 and 256. A preferred method of forming this embodiment is to provide two cylindrical billets and to place a first of them over a mandrel. Then the stent is placed over the first billet. Then the second billet is placed over the stent. Then, the two billets are bonded together, for example by sintering. Then the bonded structure, including the stent, is expanded and sintered. Finally, the sub-channel-creating material is removed (e.g. salt) and the drug material inserted. Note that the sub-channels 250, 253 of either layer 251, 256 can be provided with reinforcements, drugs, medicaments, or any combination of these.

In an alternative embodiment, the tubes can be expanded before laminating to the stent. In another alternative, the salt or other included material is removed prior to expansion and/or prior to sintering.

The embodiment 264 has an outer layer outer layer 261 and an inner layer 266, but only the inner layer is a composite with drug-containing sub-channels 263. The outer layer 261 is a monolithic material. The inner layer 266 defines a channel 271. The other structure 252, as in the previous embodiment, is preferably a stent, which is secured between the composite structure layers 261 and 266. In alternative variations of this embodiment, the sub-channels 263 could be switched between the outer layer 261 and the inner layer 266 so that the outer layer 261 had sub-channels with, for example, a drug, and the inner layer 266 was of monolithic material. In another embodiment, the monolithic layer of either of the above embodiments could be left out so that the stent is exposed on a respective side.

A preferred method of forming this embodiment is to provide one cylindrical billet as shown in FIG. 2A and to place it over a mandrel. Then the stent is placed over the billet. Then the monolithic tube is placed over the stent. Then, the billet and monolithic layer are bonded together, for example by sintering. Then the bonded structure, including the stent, is expanded and sintered. Finally, the sub-channel-creating material is removed (e.g. salt) and the drug material inserted. In an alternative embodiment, the tubes can be expanded before laminating to the stent. Note that the sub-channels 253 can be provided with reinforcements, drugs, medicaments, or any combination of these. Also, note that the sub-channels can be provided in either the outside or inside layer.

Figure 3B:
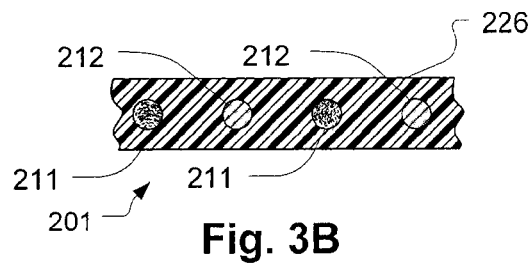

FIGS. 3A and 3B show flat structures which are similar to the structures of FIGS. 1A to 1E, except for their shapes which could be any kind of flat structure. Although two structures are shown, any of the embodiments discussed with reference to FIGS. 1A to 1E can be provided in a flat equivalent, which may be considered a planar development of the cylindrical shape. A wall 220 of biocompatible material such as PTFE has a planar array of channels 210 which contain a drug material. In alternative embodiments, these channels 210 can contain any desired mix of materials. For example, in the embodiment 201, the channels 211 and 212 alternately contain drug material (channels 211) and reinforcing material (channels 212), such as metal. The alternating array structure of the 201 embodiment can also be applied to the embodiments of FIGS. 1A to 1E.

The structures of FIGS. 3A and 3B can be made in the same way as described for the embodiment of FIG. 1A. That is, PTFE and granular salt may be co-extruded, with the salt defining the sub-channels, to form a flat billet. The billet may then be expanded and sintered and the salt dissolved with water to form an article with open sub-channels. The drug may be inserted in the sub-channels, for example, by injecting microsphere-encapsulated drug particles or by threading a drug-impregnated fiber through the sub-channels.

Figure 4A:
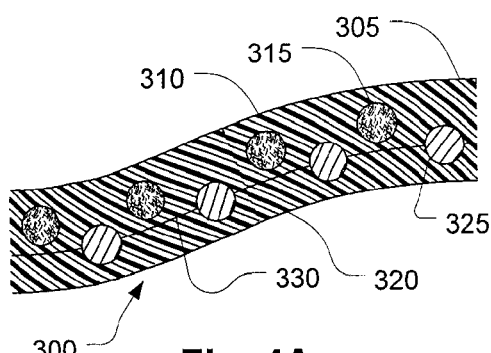
FIGS. 4A through 4D illustrate various wall portions of grafts having various structures similar to the embodiments of FIGS. 1A-1E.

FIGS. 4A to 4D represent wall portions of arbitrary structures, which may be cylindrical, flat, non-circular cylinders, cones, or any desired type of open or closed structure. Referring to FIG. 4A, a graft 300 has two layers 305 and 320 that are laminated to each other. In this embodiment, a first array of channels 315, which carry a drug (but which could contain a reinforcement or other material), is contained in the layer 305. Another layer of material 320 is a monolithic layer. Another structure 325, for example a woven layer of metal reinforcement filaments, is sandwiched between the two layers 305 and 320.

A preferred method of forming this embodiment is to provide one billet with the appropriate shape, for example, a flat patch. Then the additional structure, for example, a woven reinforcement layer is placed onto this billet. Then the monolithic layer is placed over it and bonded through the woven reinforcement with the other layer, for example by sintering. Then the bonded structure, including the additional structure, is expanded and sintered. Finally, the included spacing material is removed (e.g. salt) and the drug material or reinforcement material inserted.

Figure 4B:
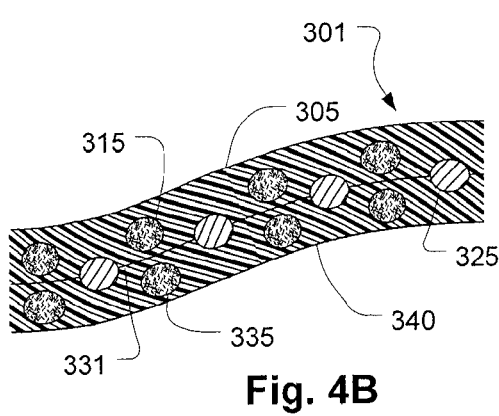

Referring to FIG. 4B, a graft 301 has two layers 305 and 340 that are laminated to each other. In this embodiment, a first array of channels 315, which carry a drug (but which could contain a reinforcement or other material), is contained in the layer 305. Another layer of material 340 has a second array of channels 335, which carry also carry a drug (but which could contain a reinforcement or other material). Another structure 325, is the same as for the previous embodiment 300.

A preferred method of forming this embodiment is the same as for the embodiment 300 except that the method laminates two composite billets which include material holding the channels open rather than a composite billet and a monolithic billet.

Figure 4C:
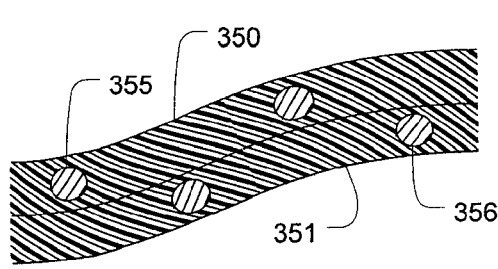

Referring to FIG. 4C a graft 353 has two layers 350 and 351, both of which are composite layers with reinforcement material within the sub-channels 355 and 356. The preferred method of making the embodiment 353 is substantially similar to the foregoing embodiments 300 and 301. The embodiment 357 shown in FIG. 3d has different materials in the channels 355 and 365, those being drugs and reinforcements. In other respects this embodiment is as the embodiment 353.

Figure 4D:
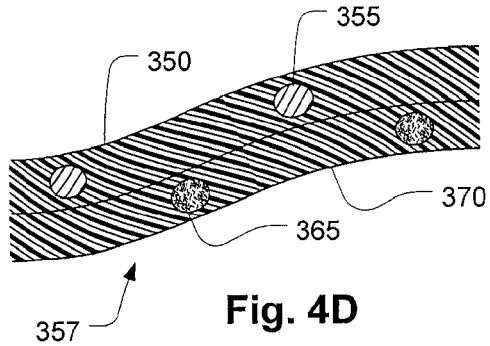
Figure 4E:
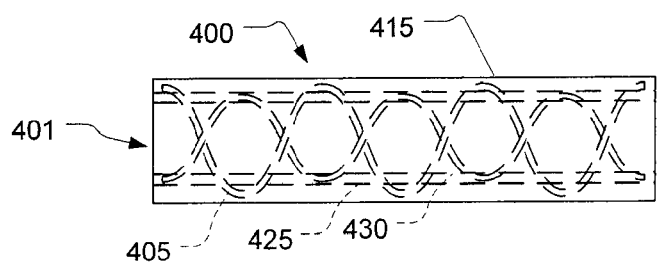
FIG. 4E illustrates a tubular graft with counter-twisting helical channels according to another embodiment of the invention.

Referring to FIG. 4E, an embodiment of a tubular graft 400 is consistent with the embodiments 353 and 357 of FIGS. 4C and 4D, but has, specifically, a tubular structure. In this structure, the sub-channels 405 and 430 are helical in shape, which can provide certain benefits, depending on the application. For example, helical reinforcements provide a degree of hoop and longitudinal stress 30 compensation which may be desirable. Also, the helical shapes of the sub-channels 405 and 430 are in opposite directions to cancel out any twisting moment that might be generated under axial load. As in the embodiments 353 and 357, there are two composite structure layers 415 and 425.

A preferred method of forming the embodiment 400 is to provide two cylindrical billets as shown in FIG. 2A and to place the first of them over a mandrel. After supporting on the mandrel, the first billet is twisted to cause the sub-channels to adopt a helical shape. The same is done with the second billet so that its sub-channels have a helical shape, which is subsequently removed from its respective mandrel. Optionally, next, a stent is placed over the billet on the first mandrel. Then the other cylindrical composite billet is placed over the first billet or the stent. Then, the billets are bonded together, for example by sintering. Then the bonded structure, which may include the stent, is expanded and sintered. Finally, the included spacing material is removed (e.g. salt) and the drug or reinforcing material inserted. Note that the sub-channels 405 and 430 can be provided with reinforcements, drugs, medicaments, or any combination of these.

In all of the foregoing embodiments, after materials are added to the sub-channels or channels, such as reinforcements or drugs, the ends of the sub-channels or channels may be sealed to prevent leakage or to cover the ends of any reinforcing members.

FIG. 5 is an embodiment of a method for creating the embodiments of the invention described above. The method starts with two different techniques for creating an unexpanded billet with channels (M30) within the biocompatible polymer matrix. The first, a preferred technique, is to co-extrude the polymer and the included material to form the billet which is later expanded and sintered to form the product. This operation of co-extrusion to form the billet is represented at M5. The second operation to create a composite billet is to create a pattern M10 on the surface of a billet of biocompatible polymer in either of two ways.

The first way of creating a pattern M10 is to create a pre-form structure, such as a lattice structure 500 illustrated in FIG. 6. The pre-form is then laminated between two monolithic (although they could be composite structures) layers of biocompatible polymer M25. This operation may include sintering or some other means of bonding the two layers such that the material other than that of the lattice becomes continuous between the two layers. Alternatively, other suitable techniques such as adhesive or solvent boding, can be used to secure the layers together. In that way, the lattice, can, once removed, defines channels in the matrix of the biocompatible polymer material of the graft. For example if the lattice 500 were of wax, it could be removed by low temperature heating.

Preferably, the lattice 500 provides a continuous path between all points (e.g., point 505) of the lattice 500 to edges (e.g., point 510) so that material/solvent can enter and leave the through the channels at the edges. If the pre-form material is to be removed by a solvent and the dissolved material can pass easily through the pores of the ePTFE material, continuous path may not be a requirement, although it is still preferable. Also, although the illustration 500 is generally a rectangular flat lattice, such structures may be made in cylindrical and other three and two dimensional shapes. Also, the pre-form need not be a regular structure as a lattice. It can have any suitable structure. The pre-form may be manufactured by any suitable method, for example by molding.

The second way of creating a pattern M10 is to lay a trail or bead M20 of the included material on one layer of the biocompatible polymer material. Examples of included material include wax, polymers, glass or metal fibers, divided materials including salt, metal, glass, and others. Once this pattern is formed, a second layer may be laminated to the first M25. Again, the laminating operation M25 may include sintering or some other way of bonding the two layers such that the material other than that of the pattern of included material becomes continuous between the two layers. In that way, the included material, can, once removed, define channels in the matrix of the biocompatible polymer material of the graft. Note, as with the lattice 500, preferably, the pattern provides a continuous path to all points to the ends to enhance removal of the included material.

The result of the above is an unexpanded billet with channels as indicated at M30. Note that the discussion of the embodiments of FIGS. 1A through 4E have identified the channels incorporated billet (intermediate product) and finished article as channels and sub-channels. The channels and sub-channels need not be tubular (e.g., with only two endpoints) in structure. They can have multiple interconnecting structures with varying cross-sectional areas at points and so on. In fact, referring to FIG. 7, the M10 technique can be used for creating internal capsules 520 within the graft. Such an internal capsule 520 could be isolated, or partially isolated, from the external surface 530 of a graft by providing a patch 535 of less permeable material between the capsule 530 and the outside surface. For example, if it were desired to store additional drug in a graft for longer term administration, without causing concentrated release in particular areas, such as the locations of the capsules 520, the patch 535 could provide this function. Note that the capsule 525 and channels 525 stemming therefrom may be part of a network of capsules and channels.

The billet may, at this point, be shaped or strained M35. For example, a co-extruded billet with sub-lumen channels could be twisted to change the channels from axilinear to helical channels as in the 400 embodiment of FIG. 4E. The billet, whether shaped in operation M35 or otherwise, may be laminated M40 to another material, another billet, or another included article, such as a stent, as discussed above with reference to the embodiments of FIGS. 1C-E, and 4A-4E. This operation of laminating M40 may involve the use of a fixture such as a mandrel. It may also involve the use of pressure-generating devices and heating devices, chemical solvents, ultrasonic welding devices, and other bonding devices as are known in the art.

In operation M45, the billet structure is then expanded and in operation M50 the expanded structure is sintered. These operations are known in the art and are not discussed in detail. In operation M55, the inserted material is removed. Operation M55 can include the dissolution of the included material, for example the pre-form or the co-extruded salt, or it can include the melting of such material or it could simply include the mechanical withdrawal of the included material such as pulling a wire from the article. In operation M60 the drug, reinforcement, or other material is inserted in the final article.

The sequence of the operations M45-M60 can be rearranged to perform the removal M55 and insertion M60 operation ahead of the expanding and sintering operations M45 and M50 if the inserted material can tolerate the expanding and sintering operations M45 and M50. Also, the operations of expanding and sintering M45 and M50 may be performed after removing the inserted material M55 or in a simultaneous process. For example, water could be used to remove sodium chloride as the included material while the article undergoes the expansion.

The removal operation M55 may include extraction of the material by withdrawing it, such as if the included material is a fiber or filament. Alternatively, it may include dissolving the material using a solvent. Yet another alternative is to remove the material by changing its properties. Yet another alternative is to leave a radiation curable polymer in the expanded billet and to cure it with radiation (for example electron beam or ultraviolet light) either before or after sintering. In this last alternative, the removal and insertion operations M55 and M60 can be thought of as taking place in the same curing operation.

One preferred method of inserting a drug in the expanded and sintered billet is to impregnate a yarn or filament with the drug and thread the yarn or filament through the channels. The drug may be microencapsulated to help ensure its bioactivity. Another method is to inject the drug, which may be mixed in a liquid medium, into the channels using a catheter or needle.

It is possible to include the drug in the manufacture of the graft from the beginning, at least for drugs that can tolerate the sintering while maintaining their bioactivity. An example of such a drug is silver nitrate. In such a case, a drug material can be combined with the biocompatible polymer to form a billet in step M5 or M10-M25 and the billet M30 can be expanded and sintered. Obviously, many reinforcing materials could be incorporated in the billet in this way so that the subsequent steps of removing M55 and inserting M60 would not be required. In another alternative, the included material has properties such that it can remain in the channels after expansion and sintering. In such as case, the material, whether or not it is changed by the expansion and sintering or by another process, such as radiation curing, allows the insertion of a drug into the channels occupied by it. For example, if the material ultimately left in the channels permits drugs to be injected or, perhaps better, if it can effectively wick the drug into the channels, then the desired results can be achieved without performing the removing M55 and insertion M60 operations either.

In addition to the materials, it is possible for the surface characteristic of the graft 100, 220 to remain unaffected by the inclusion of these materials in the sub-channels 110, 210. For example, even if a material in the sub-channels 110, 210 has an undesirable texture, for example, a coarse texture, the surface texture of the graft 100, 220 can be completely different, for example a smooth texture.

Using the above methods, grafts of extremely small size can be made. For example, tubular grafts whose diameter is as small as 1 mm. can be manufactured.

In all of the above embodiments involving extrusion, the PTFE is preferably mixed with a lubricant.

An example of a method for making a particular embodiment is described below.

1. Prepare a mixture containing PTFE and lubricant, for example the ratio of 83 grams of PTFE powder resin to 17 grams of Isopar H lubricant. Preferably this is incubated, for example for a period of 2 hours.
2. Grind a removable material for defining the sub-channels. For example, this may be sodium chloride in a preferred embodiment. Preferably this is sieved to provide a particle size fraction less than 100 μm.
3. The removable material is preferably combined with a lubricant. For example, 86 grams of sieved sodium chloride powder may be mixed with 17 grams of Isopar H, which may be incubated for 2 hours.
4. An extrusion die is provided which has the required geometry for the extruded billet prior to expansion. In an embodiment, billet may have 30 μm to 4000 μm thick tubes. Preferably, the size range is 50 μm to 1000 μm.
5. The PTFE and removable material mixtures are then extruded.
6. After extrusion, expose the billet to water to dissolve the sodium chloride.
7. Continue expansion and sintering according to techniques known in the ePTFE vascular graft manufacturing art.

Note that, in an alternative, steps 6 and 7 can be switched.

In step 8, the water, to which the billet is exposed, may be heated to accelerate dissolving of the sodium chloride. In addition, a water batch may be agitated or recirculated continuously to accelerate the dissolving of the sodium chloride. Soluble materials other than sodium chloride may also be used. Although the exemplary method employs using polytetrafluoroethylene, other materials, such as polymeric materials, may also be used. Although in the exemplary embodiment, the sodium chloride particle size was reduced to 100 μm or less, the particle size may be adjusted, for example, to adjust the surface roughness of the sub-channel walls.

The above described method embodiment may be used to impart a selectable degree of surface roughness to the sub-channel walls. For example, an isotropic roughness of 100 μm, may be imparted. Also, note that the above method embodiment is presented merely as an illustrative example and is not intended to limit the scope of the invention.

In some applications, for example applications where drugs are to be administered slowly over time from the sub-channels, a roughened surface may be desirable in the interior surfaces of the sub-channels. The use of granular material creates channel to define the sub-channels in the extruded tube may impart such a roughened surface structure as illustrated in FIG. 2B. The grain size of the sodium chloride may be selected to determine the surface roughness characteristic. For example, an isotropic roughness of 100 μm, may be imparted. Although in the exemplary embodiment, the sodium chloride particle size was reduced to 100 μm or less, the particle size may be adjusted, for example, to adjust the surface roughness of the sub-channel walls. Note that the precise size and shape of the channels may be selected for a given application.

The channel may be filled with bioactive compounds that show anti-restenosis activity such as Rapamycin® or Paclitaxel® and antibiotic such as rifampin to control the infection. If desired, the bioactive compound may be first loaded into a polymeric carrier such as degradable polyesters to control its release. The polymeric carrier may be in the form of a fiber, filament, rod or microspheres.

If desired the channels may be filled with nitinol wires to make a stent graft which can be delivered using methods known in interventional cardiology. Also, instead of sodium chloride, the channels may be defined by other materials which may be removed by other means. For example, a wax may be used which may be removed after extrusion by melting it.

Details on manufacturing porous PTFE tubing generally, are described, for example, in U.S. Pat. Nos. 3,953,566, 3,962,153, and 4,973,609, the entireties of which are herein incorporated by reference.

In a typical method, a PTFE tube may be formed preparing a PTFE paste, extruding the article (e.g., tube), expanding the article, and sintering it. A PTFE paste dispersion may be made for later extrusion by admixing virgin PTFE powder such as Fluon® CD123 PTFE Coagulated Dispersion Powder from Asahi Glass Co., F-104, F-103, virgin PTFE fine powder with a liquid lubricant. Examples of lubricants are mineral spirits or naphtha to form a paste of a desired consistency. The paste may either forced through an extrusion dye or coated onto a mandrel. The wet extrudate may be dried by evaporating the lubricant. After drying, the material may be stretched (elongation) and/or expanded in other directions. The stretching/expansion step may be done at temperatures in the range of 250-325 C. Expansion rates of two to one (2:1) are typical. The extrudate may then be sintered by heating it to a temperature of about 350-370 C creating an amorphous locking of the polymer.

Reinforcement fibers or structural materials such as nitinol, may be threaded through the sub-channels 110, 210 to make a finished article. In addition, before or after the threading (or the addition of drugs), the finished article may be twisted so that the channels are formed into a helical sub-channels. This may be desirable where reinforcement in the radial and axial directions are required.

In all of the foregoing method embodiments, there are many materials that can be incorporated in a billet (including an expanded billet) and used with the various methods described in the present disclosure. Examples of these include: hyaluronic acid, polyethylene-oxide, polyvinyl-alcohol, dextran, gelatin, and cellulose.

In all of the embodiments drugs may be used in the channels or voids, as mentioned. In such embodiments, a particularly useful class of drugs is anesthetics. Grafts are often attached to, or positioned close to, traumatized tissue. The trauma may be a result of the attachment of the graft or as a result of another related or unrelated procedure. By including an anesthetic, alone, or in combination with other drugs or reinforcement materials in the sub-channels or chambers, the effects of the trauma can be mitigated. Also the anesthetic can be delivered in a manner that concentrates it where it is needed most.

In addition to graft embodiments, the embodiments cover non-graft devices such as patches or cylinders or other extrudable shapes can be used purely for the purpose of delivering one or more drugs to a site within a living host. For example, such a device may be removable, such as a drain left in a patient after surgery to allow fluid to exit. Such a drain may deliver drugs or be reinforced in the manner described in the instant application. Also, the device need not serve a function other than drug-delivery. For example, it may be left in a patient purely for the purpose of delivering drugs without serving an additional function, such one of a graft.

In all of the embodiments, the invention does not preclude the combination of the inventive embodiment with other devices and even such combinations that cause another article to come between the inventive device and the host tissue. For example, a cylindrical medical device with sub-channels that hold drugs may be placed over a catheter or graft whose interior contacts blood or other fluids from the host and the medical device with the sub-channels is attached to provide a vehicle for drug delivery.

In the foregoing embodiments, various kinds of drugs, medicaments, or agents may provided in the disclosed channels and/or chambers. Examples include, non-genetic therapeutic agents such as anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, cell cycle inhibitors and activators inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; cytostatic or cytotoxic and agents which interfere with endogenous vascoactive mechanisms.

Genetic materials may also be used such as anti-sense DNA and anti-sense RNA as well as other molecules working via the same mechanism of transcriptional or translational inhibition or activation. Genetic material also include (sense) DNA or (sense) RNA or equivalents thereof coding for Genes to replace defective or deficient endogenous molecules or increase their amount or stability, or encode for non-endogenous or endogenous modified molecules with biological effects. Genetic material also includes nucleic acids affecting Gene expression or other cellular mechanisms by other ways than described above. Such Genetic materials could be organized "naked," packed with supporting molecules or in form of viruses or other vectors. Genes and their expression affected by above Genetic materials include but are not restricted to: tRNA or rRNA angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors and activators including CD inhibitors, thymidine kinase ("TK") and other agents useful for interfering with cell proliferation, transcription factors, translation factors, the family of bone morphogenic proteins ("BMP's"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA encoding them.

While the present invention has been disclosed with reference to certain preferred exemplary embodiments, numerous modifications, alterations, and changes to the described exemplary embodiments are possible without departing from the sphere and scope of the present invention. Accordingly, it is intended that the present invention not be limited to the described exemplary embodiments, but that it have the full scope defined by the language of the following claims and equivalents thereof.

The invention claimed is:

1. A method of forming a medical device, comprising:
   co-extruding a first material and a second material into a cylinder of the first and second materials, such that, after extrusion, the second material defines at least one elongate structure extending generally along a length of the medical device surrounded by the matrix of the first material; and
   prior to implantation of the medical device within a patient removing the second material from the first material to leave a void in the first material;
   twisting the cylinder such that the voids left in the first material, after removal of the second material, are formed into helices;
   inserting a reinforcement filament into the voids left in the first material; and
   forming the medical device into a vascular graft.

2. The method of claim 1 wherein the second material is granular with a particle size of not more than 100 μm.

3. The method of claim 1 wherein the second material is a soluble material and the removing includes dissolving the soluble material.

4. The method of claim 1 further comprising expanding the first material after removing the second material.

5. The method of claim 1 wherein the first material includes polytetrafluoroethylene.

6. The method of claim 1 further comprising filling the voids left in the first material, after removal of the second material, with a drug.

7. The method of claim 1 further comprising filling the voids left in the first material, after removal of the second material, with an antithrombogenic drug.

8. The method of claim 1 further comprising filling the voids left in the first material, after removal of the second material, with a drug/polymer mixture.

* * * * *